US009174339B2

(12) United States Patent
Goldfarb et al.

(10) Patent No.: US 9,174,339 B2
(45) Date of Patent: Nov. 3, 2015

(54) CONTROL SYSTEM FOR A GRASPING DEVICE

(75) Inventors: Michael Goldfarb, Franklin, TN (US); Skyler Dalley, Nashville, TN (US); Huseyin Atakan Varol, Astana (KZ)

(73) Assignee: VANDERBILT UNIVERSITY, Nashville, TN (US)

( * ) Notice: Subject to any disclaimer, the term of this patent is extended or adjusted under 35 U.S.C. 154(b) by 152 days.

(21) Appl. No.: 13/988,820

(22) PCT Filed: Nov. 21, 2011

(86) PCT No.: PCT/US2011/061698
§ 371 (c)(1),
(2), (4) Date: May 22, 2013

(87) PCT Pub. No.: WO2012/071343
PCT Pub. Date: May 31, 2012

(65) Prior Publication Data
US 2013/0253705 A1    Sep. 26, 2013

Related U.S. Application Data

(60) Provisional application No. 61/416,078, filed on Nov. 22, 2010.

(51) Int. Cl.
*B25J 9/02* (2006.01)
*A61F 2/72* (2006.01)
(Continued)

(52) U.S. Cl.
CPC . *B25J 9/02* (2013.01); *A61F 2/583* (2013.01); *A61F 2/72* (2013.01); *A61B 5/04888* (2013.01);
(Continued)

(58) Field of Classification Search
CPC ............. A61F 2/68; A61F 2/72; A61F 2/583; A61F 2/386; B25J 15/0009; B25J 15/10; B25J 9/0006; B25J 9/1612; A61B 5/04888; A61B 5/225
See application file for complete search history.

(56) References Cited

U.S. PATENT DOCUMENTS 7,828,857 B2 * 11/2010 Farnsworth et al. ............ 623/64
2008/0188952 A1 * 8/2008 Veatch et al. ................... 623/57

FOREIGN PATENT DOCUMENTS

WO    2008098072 A2    8/2008
WO    2011022572 A1    2/2011

OTHER PUBLICATIONS

Ciprani et al., "On the Shared Control of an EMG-Controlled Prosthetic Hand: Analysis of User-Prosthesis Interaction", IEEE Transactions on Robotics, Feb. 1, 2008, vol. 24, No. 1, pp. 170-187.
(Continued)

*Primary Examiner* — Khoi Tran
*Assistant Examiner* — Robert Nguyen
(74) *Attorney, Agent, or Firm* — Novak Druce Connolly Bove + Quigg LLP

(57) ABSTRACT

A method for operating a grasping device and grasping devices therefrom are provided. The grasping device is configured to use a plurality of parallel, bi-directional state flow maps each defining a sequence of poses for a plurality of joints in the grasping device. The method include receiving at least one control signal, determining a current pose of the grasping device within the one of the plurality of state flow maps currently selected for the grasping device, and selectively actuating the plurality of joints to traverse the sequence of poses, where a direction for traversing the sequence of poses is based on the at least one control signal.

18 Claims, 7 Drawing Sheets

(51) Int. Cl.

| | |
|---|---|
| A61F 2/58 | (2006.01) |
| B25J 9/16 | (2006.01) |
| B25J 9/10 | (2006.01) |
| B25J 15/10 | (2006.01) |
| A61F 2/68 | (2006.01) |
| B25J 15/08 | (2006.01) |
| A61B 5/11 | (2006.01) |
| A61B 5/0488 | (2006.01) |
| B25J 15/00 | (2006.01) |
| A61F 2/70 | (2006.01) |
| A61F 2/76 | (2006.01) |

(52) U.S. Cl.
CPC .. *A61B 5/11* (2013.01); *A61F 2/586* (2013.01); *A61F 2/68* (2013.01); *A61F 2002/587* (2013.01); *A61F 2002/6872* (2013.01); *A61F 2002/704* (2013.01); *A61F 2002/764* (2013.01); *A61F 2002/7625* (2013.01); *A61F 2002/7635* (2013.01); *B25J 9/10* (2013.01); *B25J 9/1612* (2013.01); *B25J 15/0009* (2013.01); *B25J 15/08* (2013.01); *B25J 15/10* (2013.01); *Y10S 901/15* (2013.01)

(56) References Cited

OTHER PUBLICATIONS

D. P. J. Cotton et al., "Control strategies for a multiple degree of freedom prosthetic hand", UKACC Control 2006 Mini Symposia, Jan. 1, 2006, pp. 211-218.

International Search Report and Written Opinion mailed Mar. 23, 2012. In corresponding application No. PCT/US2011/061698.

* cited by examiner

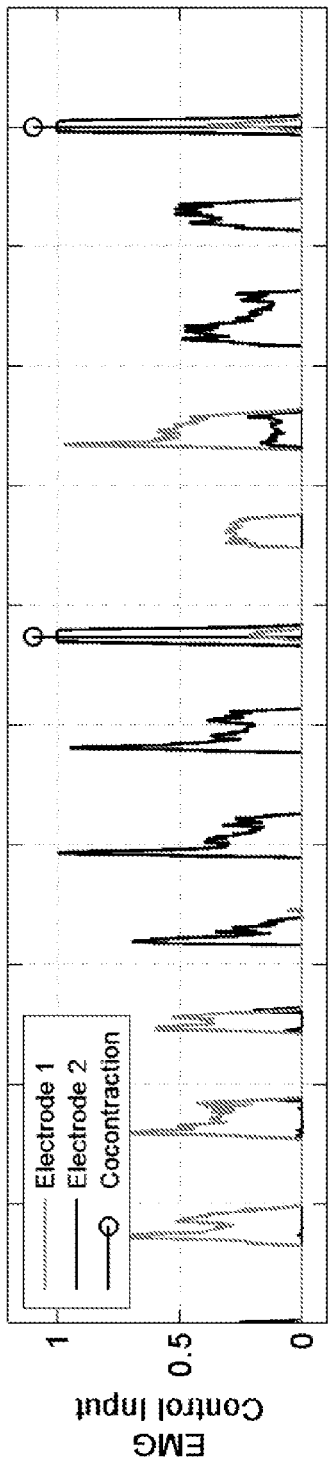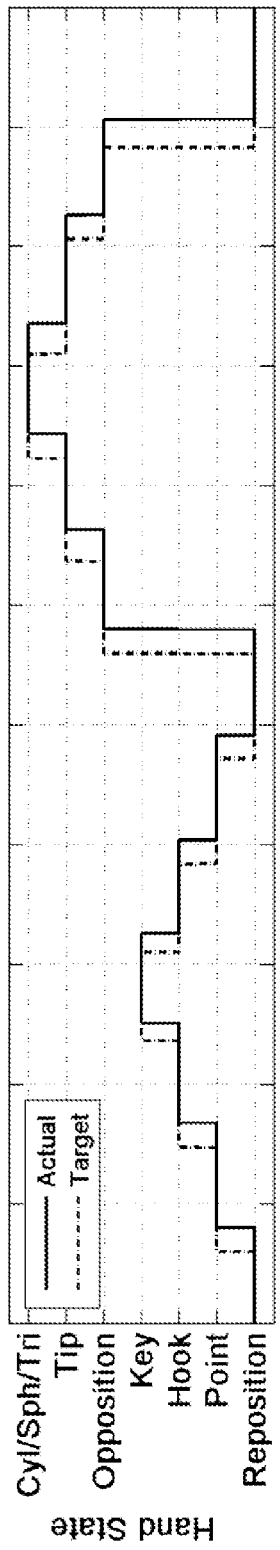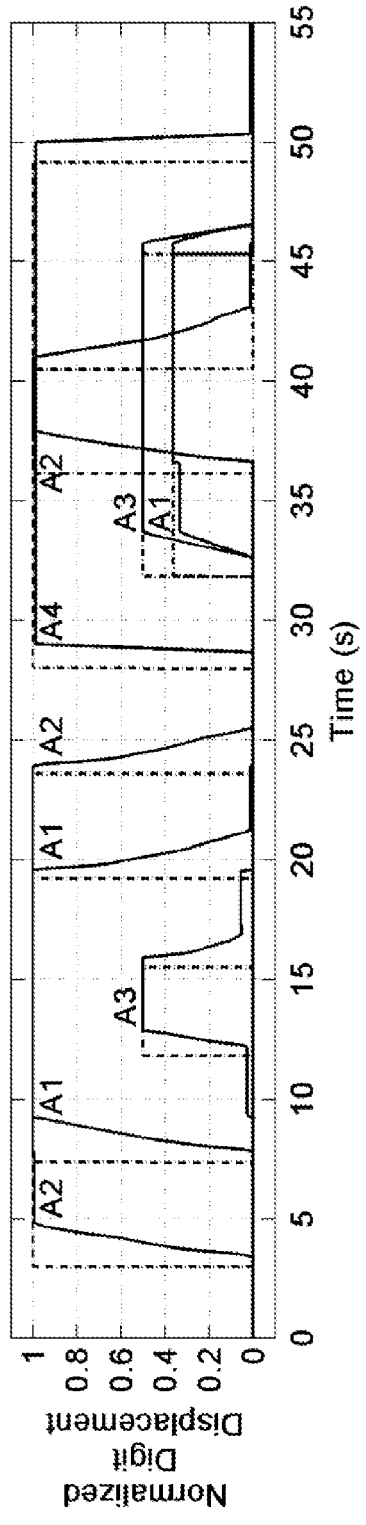

CONTROL SYSTEM FOR A GRASPING DEVICE

CROSS-REFERENCE TO RELATED APPLICATIONS

This application is a §371 national stage entry of International Application No. PCT/US2011/061698, filed Nov. 21, 2011, which claims priority to U.S. Provisional Application No. 61/416,078, filed Nov. 22, 2010, both of which are hereby incorporated by reference.

FIELD OF THE INVENTION

The present invention relates to grasping devices, and more specifically to a control system for grasping mechanical devices.

BACKGROUND

Grasping mechanical devices, such as robotic prosthetic devices, for simulating and replacing natural limbs and appendages have been in use for decades. However, the design and operation of such devices generally fail to simulate an appreciable number of the discrete movements of these natural limbs and appendages. For example, hand prosthetic devices range from a passive type, which simulate the appearance of a natural hand but do not move, to newer myoelectric devices, having various combinations of pulleys, cables, linkages and the like with battery-powered operating and control systems, controlled by electromyogram (EMG) signals generated by muscles in a residual limb. In general, these conventional hand prosthetic devices include only a hook or cooperating digits which can grasp an object between them. As a result, they are generally incapable of other grasps or postures. Although, the ability to grasp and hold objects can be a significant improvement for the lifestyle of a hand and/or arm amputee, such amputees are often dissatisfied with the limited utility of such prosthetic devices.

SUMMARY

Embodiments of the invention concern control systems for grasping devices. In a first embodiment of the invention, a method for operating a grasping device using a plurality of parallel, bi-directional state flow maps each defining a sequence of poses for a plurality of joints in the grasping device is provided. The method includes receiving at least one control signal and determining a current pose of the grasping device within the one of the plurality of state flow maps currently selected for the grasping device. The method also includes selectively actuating the plurality of joints to traverse the sequence of poses, wherein a direction for traversing the sequence of poses is based on the at least one control signal.

In a second embodiment of the invention, a method for operating a grasping device using a plurality of parallel, bi-directional state flow maps each defining a sequence of poses for a plurality of joints in the grasping device is provided. The method includes receiving at least one electromyogram (EMG signal) and obtaining a current mechanical state of the grasping device, a current state flow map from the plurality of state flow maps, and a current position of the grasping device within the current state flow map. The method further includes actuating the plurality of joints to transition to at least a next pose in the sequence of poses in a selected direction based on the at least one EMG signal.

In a third embodiment of the invention, a grasping device is provided. The grasping device includes a plurality of joints and a memory for storing a plurality of parallel, bi-directional state flow maps that each defining a sequence of poses for the plurality of joints. The grasping device further includes a processor communicatively coupled to the memory and the plurality of joints. The processor is configured for receiving at least one control signal and determining a current pose of the grasping device within the one of the plurality of state flow maps currently selected for the grasping device. The processor is also configured for selectively actuating the plurality of joints to traverse the sequence of poses, where a direction for traversing the sequence of poses is based on the at least one control signal.

Additionally, other embodiments of the invention include a computer-readable medium having stored thereon instructions for carrying out any of methods and systems described herein.

BRIEF DESCRIPTION OF THE DRAWINGS

FIG. 6A is an X-Y plot of EMG input as a function of time for a hand device configured in accordance with an embodiment of the invention.

FIG. 6B is an X-Y plot of hand state or pose as a function of time, showing targeted (dashed line) and actual (solid line) poses.

FIG. 6C is an X-Y plot of normalized digit displacement as a function of time for actuators A1 (index finger (DII) flexion/extension actuator), A2 (middle, ring, and little finger (DIII-V) flexion/extension actuator), A3 (thumb (D1) flexion/extension actuator), and A4 (thumb (D1) abduction/adduction actuator).

DETAILED DESCRIPTION

Figure 1:
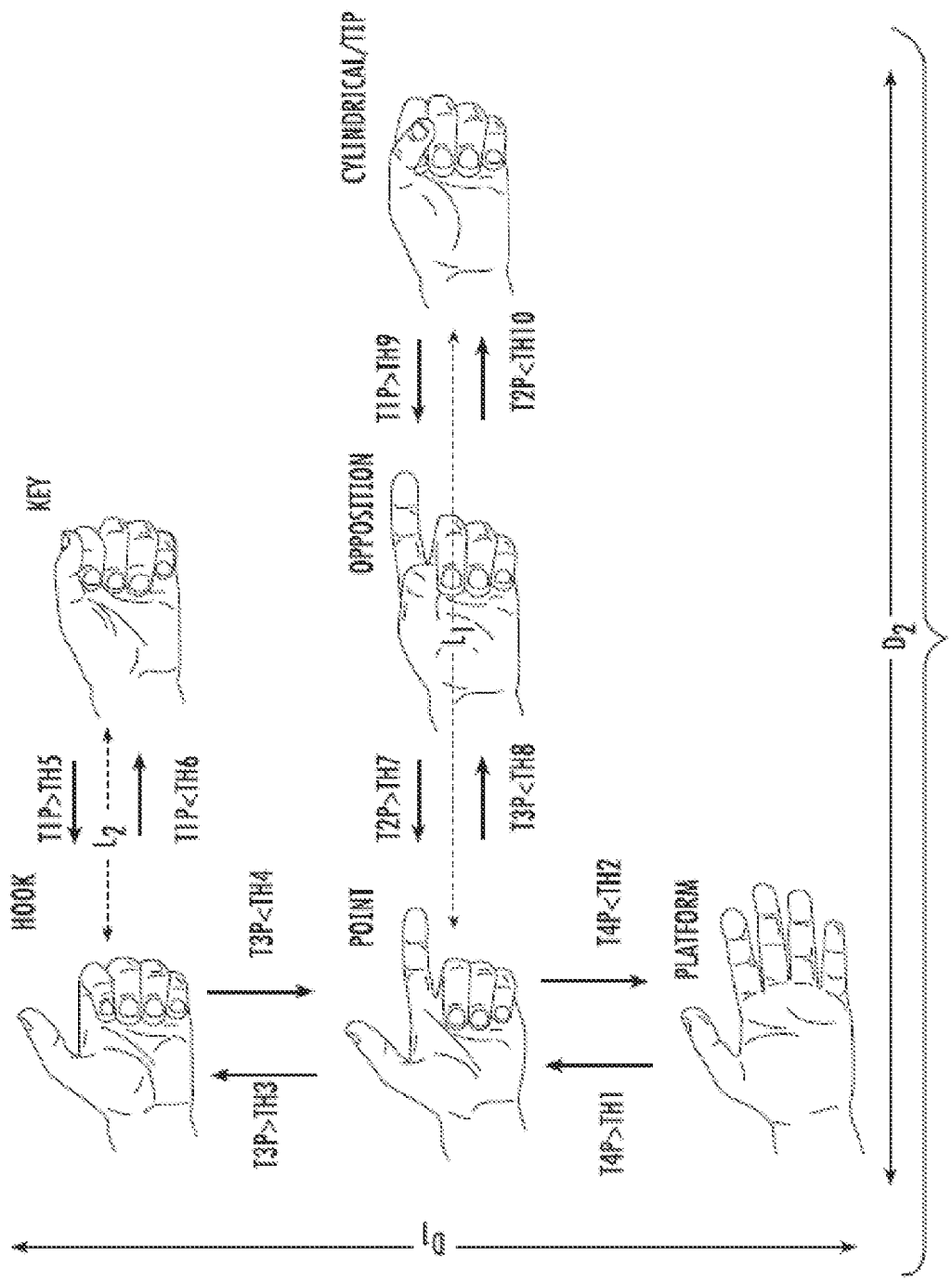
FIG. 1 shows an topographic state map that is useful for describing the various embodiments of the invention.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

Conventional control methods for jointed mechanical devices, particularly robotic prosthetic devices, are generally classified into one of two groups: pattern recognition methods and direct control (non-pattern recognition) methods. The term "jointed mechanical device" as used herein, refers to any powered mechanical device having one or more movable joints, including, but not limited to, robotic prosthetic and robotic non-prosthetic devices. In direct control methods, two EMG signals are generally required to actuate each joint in the device (i.e., one EMG site for each direction of motion). However, in conventional prosthetic devices, such as myoelectric prosthetic devices, the number of independent inputs available is generally limited, and consequently, direct control methods provide simultaneous control of only one or two degrees of freedom. As a result, direct control methods are generally useful in only simpler prostheses with few active joints.

In pattern recognition methods, the device is switched between various discrete states based on a determination of the user's intent. For example, in the case of a myoelectric prosthetic device, the control system monitors multiple EMG signals from different muscle groups in the residual limb. If the control system detects a pattern in the muscle groups from the multiple EMG signals, a grasp or pose of the device associated with the detected pattern is selected. As used herein, the terms "grasp" or "pose" refer to a particular configuration of the joints in a jointed mechanical device. Based on this selected pattern, the device is reconfigured to provide the associated pose. Although such a method permits simultaneous control of a large number of joints, this method also has several drawbacks. First, the user is limited to only the grasps or poses configured by the control system. As a result, users do not have the ability to independently or directly control the joints in the device. Second, such methods are generally unreliable. In general, such EMG signals can vary over time. Accordingly, the pattern that needs to be recognized can also vary over time. As a result, additional maintenance and reprogramming of these devices is needed on a more frequent basis as compared to direct control devices.

To overcome the limitations of these conventional methods, embodiments of the invention provide a novel control methodology which allows continuous control of joints for high degree of freedom (>2) jointed mechanical devices. In the various embodiments of the invention, the actuation of joints in the device is not only based on the input signals (e.g., an EMG signal or other control signal), but also on the current mechanical state or status of the device. The term "mechanical state" refers to the instant configuration of joints in a jointed mechanical device. That is, the user-generated direct control signals are used to drive the device between two or more pre-defined related poses. Additionally, the control is continuous, meaning that a progression from one pose to another can be halted and/or reversed at any time. As a result, the direct user control of the individual joints is provided (an advantage of direct control methods), while allowing a complex multi-joint device to be controlled with only a few control signals (an advantage of pattern recognition methods).

Previous attempts to provide this type of control have generally relied on the use of the direct control signals to drive a device from pose to pose, where the poses and the transitions from pose to pose are pre-defined using a topographic state map with multiple motion axes. The term "topographic state map" as used herein, refers to a collection of associated poses of device, where a transition from a first pose to an adjacent or proximal pose in the topographic state map requires only a small or gradual change in the configuration of joints in the device. In such methods, the topographic state maps used typically have multiple motion axes and a plurality of transitions, where each of the transitions is in parallel with one of said motion axes and each of the motion axes is associated with complementary types of motion in said device (e.g., up/down, left, right). An exemplary topographic state map used in such methods is shown in FIG. 1.

As shown in FIG. 1, the poses are arranged along two motion axes, D1 and D2, where each motion axis is presumably associated with a bi-directional EMG input (i.e., a pair of EMG signals associated with an antagonist muscle pair). Thus, to drive the device to from a first pose to a second pose, such as from a platform pose to a cylindrical/tip pose, a first EMG signal is generated to drive the device along motion axis D1 in order to transition between the platform pose to the point pose or line L1. Thereafter, a second, different EMG signal is provided to drive the device along motion axis D1 and line L1 to transition from the point pose to the cylindrical/tip pose. The EMG signals for the respective antagonistic muscle groups would be used, in a reverse order, to return the device along the reverse path, to its original configuration. A similar process can then be utilized to transition between other poses.

While the use of a topographic state map, such as that in FIG. 1, provides a usable control methodology for the device, there are still several problems with this type of control methodology. Most significantly, the control requires two bidirectional inputs, which if provided with EMG, requires four EMG channels (or electrodes). Each additional EMG channel generates a greater degree of coupling between channels, and therefore makes control less robust. That is, although four EMG electrodes can be placed around the forearm, it is difficult for a user to generate EMG on one of these, without generating EMG on at least one other electrode. Although this coupling between channels can be attenuated with signal conditioning, the presence of coupling decreases the robustness of the controller, and also makes the system significantly more susceptible to error due to variation in electrode placement. The approach can also be somewhat awkward and non-intuitive, and thus can require a greater amount of training, effort, and concentration on the part of the user. For example, referring back to FIG. 1, to transition between poses, the user is first required to identify the target pose, identifying what transitions are required along motion axes D1 and D2, and then generate the appropriate EMG signals to effect the necessary transitions. Thus, in general, at least two different control inputs are required to achieve most postures, therefore requiring more cognition and effort on the part of the user, and also requiring more time to achieve a given posture or grasp. It should also be noted that a method that requires more than two EMG channels largely excludes the possibility of transhumeral embodiments, since transhumeral amputees generally provide at most two independent EMG signals (i.e., biceps and triceps muscle groups). Further, the movements along the respective D1 and D2 axes are not generally associated with the muscle groups generating the EMG signals. In contrast, the simple grasp and release action of a standard (single-grasp) myoelectric hand uses two electrodes, which are associated with grasp and release in the native hand, and therefore provide intuitive control of the prosthesis. Also, the use of two electrodes ensures minimal coupling between them, and enhances robustness of variation in electrode placement.

In view of the existing problems with control methodologies relying on topographic state maps, such as those shown in FIG. 1, the various embodiments provide a new control methodology that enables the user to access the multifunctional capability of the hand in a natural and efficient manner, with a single bidirectional control input (i.e., with two channels of EMG). In particular, the various embodiments provide a control methodology relying on a state map consisting of two parallel state-flow maps, one corresponding to a reposed thumb orientation and one corresponding to an opposed orientation. The selected configuration determines which state-flow map will be followed during flexion/extension EMG commands. The user can switch between these two maps utilizing a "co-contraction" response (i.e., a simultaneous contraction of antagonistic forearm musculature). Once a state-flow map (opposed or reposed) is selected, the hand prosthesis is under direct velocity EMG control, which proportionally utilizes the ventral EMG electrode for closing of the hand and the dorsal EMG electrode for opening.

The following are some notable features regarding the ease of use (i.e., the intuitive, direct nature), efficacy, and robustness of the various embodiments:

a. The hand device is always under direct, proportional control by the same agonist/antagonist muscle pair (i.e., ventral/dorsal contraction always corresponds to direct, proportional closing and opening of the hand).

b. Once a thumb configuration (i.e., sequence of poses) is selected, all switching within each respective state-flow map is performed internally and automatically by the controller, based on internal sensing in the hand device. All such transitions are transparent to the user. As previously stated, the user simply contracts the ventral/dorsal musculature in the forearm to directly and proportionally control the speed of closing/opening the respective grasp poses.

c. The user is assumed to most commonly anticipate the type of desired grasp or pose prior to a given interaction (i.e., prior to making an arm movement). In this manner, no co-contracting is required during manipulation, such that all manipulation is controlled directly via the ventral/dorsal musculature of the forearm.

d. Co-contracting can be limited to one place in the state map (i.e., when the hand is in the platform configuration). As such, unintended co-contractions (which can occur during direct velocity EMG control) have no effect during manipulation.

e. Since objects are generally not grasped in the platform configuration, an erroneous co-contraction will not result in a dropped object. Note that, in contrast, an erroneous classification in a pattern recognition approach can result in a dropped object.

f. The orientation of the thumb provides a clear visual indication to the user regarding which of the two pose sequences the control interface is currently in, which is particularly important in the absence of other sensory feedback.

The proposed control structure, particularly the "differential" embodiment of the control structure (as discussed below), is additionally fully compatible with a standard two-site transhumeral interface. Specifically, a typical (single-grasp) transhumeral myoelectric prosthesis utilizes two EMG electrode sites, one on the bicep and one on the triceps muscles. The user uses a "co-contraction" response to switch control between the elbow joint control mode and the (single-grasp) hand control mode. Therefore, flexion of the biceps/triceps generates flexion/extension of the elbow when in the elbow control mode, and closing/opening of the hand when in the hand control mode. With the "differential" embodiment, a "co-contraction" response would be used to switch between elbow and hand control modes, and the biceps/triceps contraction would be used to control the hand in the same manner as the EMG measured from the ventral/dorsal aspects of the forearm in a transradial amputee. The approach described herein can access all poses from a single pair of electrodes, and the approach described herein requires no pattern recognition in order to map the measured EMG signals onto the directionality of the map. Rather, a differential flexion EMG measurement corresponds to a general flexion of the hand, while a differential extension EMG measurement corresponds to a general extension of the hand. This results in an intuitive control approach, such that movement of the hand from one pose to another requires very little cognition, particularly once either the reposed on opposed sequence has been selected.

The various embodiments of the invention will be described generally with respect to an exemplary embodiment of a prosthetic hand device. Further, the various embodiments of the invention will be generally described with respect to one or more particular sets of poses. However, this is for ease of understanding and illustrative purposes only. One of ordinary skill in the art will recognize that the various embodiments of the invention can be applied to any type or configuration of jointed mechanical devices using any number and types of poses.

Figure 2:
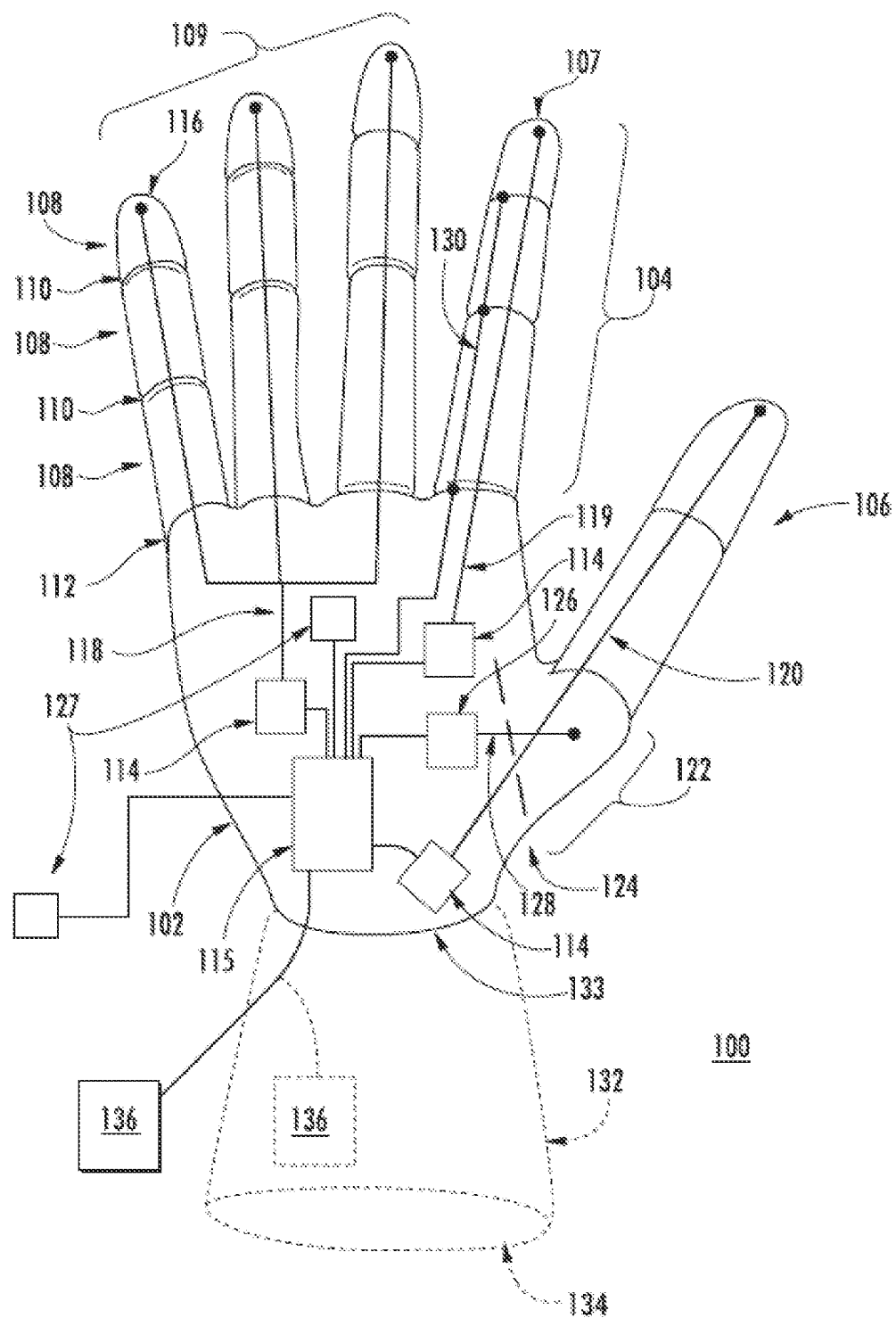
FIG. 2 is an anterior view of a prosthetic hand device in accordance with an embodiment of the invention.

FIG. 2 is an anterior view of a prosthetic hand device 100 that can be configured in accordance with an embodiment of the invention. As shown in FIG. 2, the device 100 includes a base 102 and digits comprising fingers 104, a thumb 106, or any other type of flexible or deflectable element. Each of the digits in prosthetic hand device 100 includes one or more phalangeal portions 108 interconnected by flexible joint portions 110 to allow flexing or deflection of the digits in prosthetic hand device 100. An additional flexible joint portion 112 can be used to connect the digits to base 102.

In the various embodiments of the invention, the joints referenced herein refers to any type of external or integrally formed joint device or structure that is operable to provide a connection between two portions of a device and that allows movement with one or more degrees of freedom between them. Joint devices and structures can include devices in which movement is provided via a flexible material or moving components. For example, joint devices and structures can include any type of hinge device or structure.

The digits in the prosthetic hand device 100 can be actuated using one or more force or torque actuators 114 controlled by a control system 115. The control system 115 can be coupled to one or more EMG signals to provide one or more actuation inputs to cause motion of the digits in the prosthetic hand device 100. The control system 115 can also have one or more user controls (i.e, switches, buttons, or other selection devices) or interfaces for electronically configuring its operation, as described below with respect to FIG. 5. A detailed description of the configuration and operation of the control system will be provided below with respect to FIGS. 4 and 5.

The force or torque actuators 114 are connected the distal ends 116 of the digits of prosthetic hand device 100 via one or more actuating structures coupled to the phalangeal portions 108. The actuating structures can include cable portions 118, 119, 120 attached to a phalangeal portion 108 associated with a distal end 116 of each of the digits of prosthetic hand device 100.

In the embodiment shown in FIG. 2, the prosthetic hand device 100 is configured to provide an opposable thumb. In particular, thumb 106 can be connected to base 102 via an opposable portion 122 connected to base 102 with hinge 124. This hinged portion can also be actuated using a force actuator 126 using an actuating structure including a cable portion 128 for applying a force to the opposing portion 122 and to cause it to pivot with respect to hinge 124.

In operation, the actuators 114 displace cables 118-120 (i.e., apply a force to cables 118-120), causing fingers 104 and thumb 106 to flex according to joints 110. Similarly, force actuator 126 displaces cable 128 (i.e., applies a force to cable 128), causing opposing portion 122 to flex according to hinge 124. Although the digits of prosthetic hand device 100 and opposing portion 122 could potentially flex in any direction, one of ordinary skill in the art would recognize that base 102, phalangeal portions 108, joints 110, opposing portion 122, and hinge 124 can be configured to allow motion in an anterior direction to approximate the motion of digits in a natural hand.

In some embodiments of the invention, the prosthetic hand device 100 is configured to include elastic elements in joints 110, 112, and hinge 124 to provide a restorative force when force on any of the cables 118-120 and 128 is relieved. The restorative force returns the digits of the hand device 100 to a resting position. For example, at each of the joints, a joint spring device, such as a torsion spring, can be used to provide the elastic component. However the various embodiments of the invention are not limited in this regard and, any type of spring device can be used to provide the joint spring devices.

In the embodiment shown in FIG. 2, one or more of the digits of prosthetic hand device 100 can be configured to operate in concert using a single force actuator 114. For example, as shown in FIG. 2, the thumb 106 and index finger 107 are each operated by cables 120 and 119, respectively. The other or non-index fingers 109 are configured to operate using cable 118. Such a configuration can generally be provided in prosthetic hand device 100 since independent motion of a thumb or an index finger is most common in gesturing and grasping in a natural hand. Furthermore, non-index fingers 109 typically operate in concert, also simulating typical motion in a natural hand. Such a configuration also permits a simpler configuration for control system 115, as the control of only two fingers and an opposing thumb motion is effectively required. However, the various embodiments of the invention are not limited in this regard and independent control of all digits in hand 100 can be provided.

In the various embodiments of the invention, the configuration of the force actuators 114 can be selected based on the configuration of the actuating structures. For example, for the actuating structures shown in FIG. 2 (cables 118-120), the force actuators 114 can comprise an electric motor and pulley assembly configured to operate with each of cables 118-120 of the actuating structures. Additionally, such a configuration can also include a roller clutch between a motor and a pulley in a force actuator 114. The roller clutch can be used to lock a cable of the actuating structure in place so that the configuration of the fingers 104, thumb 106, and or opposing portion 122 is also locked at a position when the motor is turned off. A similar configuration can be provided for force actuator 126 and cable 128.

In some embodiments of the invention, one or more sensors can be incorporated into various portions of hand device 100 for determining a mechanical state of hand device 100 directly or indirectly. For example, at least a portion of joints 110 can include sensors for generating signals indicative of a position of joints 110 to directly provide mechanical state information. These sensors can then be coupled to control system 115, as shown by connector 130 in FIG. 2. In another embodiment, each of actuators 114 and 126, already coupled to control system 115, can also include position sensors for providing the mechanical configuration of the device.

The force or torque actuators can also include force or torque sensing elements, which can be used to determine the force applied by hand device 100 in order to detect the presence of an object in hand device 100, and to measure the grasp force. These measurements can also be used to initiate changes between states in the state flow control system. In certain types of actuators, force or torque measurement can be provided by measuring the electrical state of the actuator. However, the various embodiments of the invention are not limited in this regard and any number of internal and/or external sensor devices 127 can be coupled to control system 115 for purposes of detecting an object in hand device 100. In such embodiments of the invention, any type of sensor device can be used, including, but not limited to mechanical, optical, or electronic sensor devices.

In some embodiments of the invention, the hand device 100 can be a portion of a larger device, such as a prosthetic arm device. In such embodiments, the hand device 100 can be mechanically coupled to at least one member 132, as shown in FIG. 2. The member 132 can be configured to attach to a residual limb or other portion of a user's body. The member 132 can include any number of movable joints, including a movable joint at joint 133 between member 132 and hand device 100. For example, as shown in FIG. 2, the member 132 can include a socket 134 for attaching member 132 to a residual limb. However, the various embodiments of the invention are not limited in this regard and member 132 can be configured to be attached to a user's body in any other way. In some embodiments, the member 132 can include sensors 136, such as EMG electrodes. However, the invention is not limited in this regard and the sensors 136 can reside external to the member 132. The configuration of the sensors 136 can be adjusted based on the particular user or source of control signals.

Figure 3:
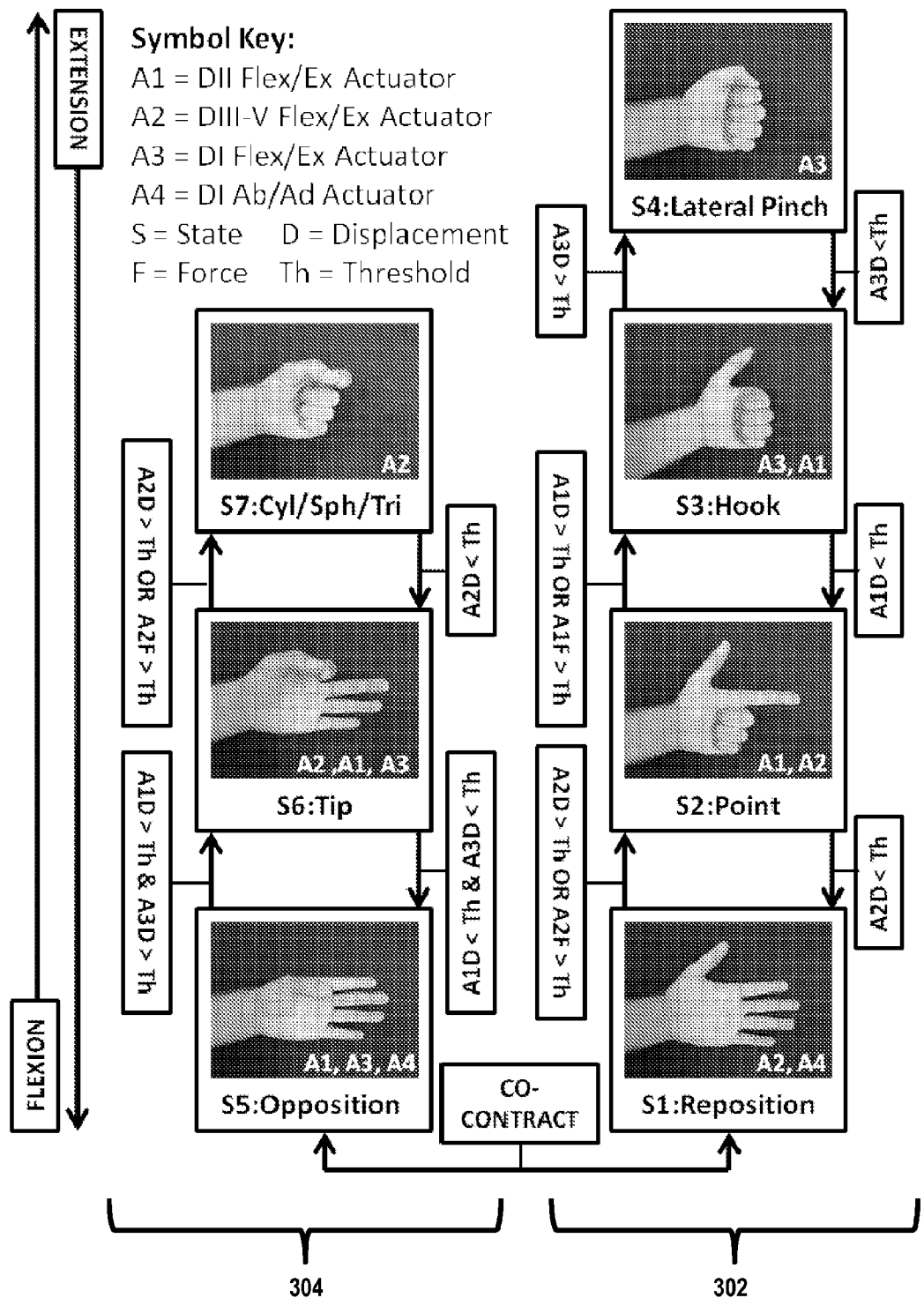
FIG. 3 shows an exemplary topographic state map in accordance with an embodiment of the invention.

FIG. 3 shows one exemplary topographic state map 300 configured in accordance with an embodiment of the invention. The control methodology corresponding to the map 300 is based on three types of EMG input, specifically flexion, extension, and co-contraction EMG signals. Based on these EMG signals and other sensory information, decisions and actions based on the sensory information intrinsic to the hand device (e.g., tendon excursions and forces) can be made. The controller can then carry out the appropriate actions (i.e., activate tendons). As noted above, the map 300 consists of two parallel state-flow maps 302 and 304, one corresponding to a reposed thumb orientation (302) and one corresponding to an opposed orientation (304). When in the platform state (in which the fingers are all extended, as shown at S1 and S5 in FIG. 3), the user selects between one of two configurations—either a platform with an opposed thumb (S5), or a platform with a reposed thumb (S1). The selected configuration determines which state-flow map will be followed during flexion/extension EMG commands. The user can switch between these two maps utilizing a "co-contraction" response (i.e., a simultaneous contraction of antagonistic forearm musculature). Once a state-flow map (opposed or reposed) is selected, the hand device is under direct velocity EMG control, which proportionally utilizes the ventral EMG electrode for closing of the hand device and the dorsal EMG electrode for opening.

As illustrated in FIG. 3, the device utilizes sensor information (on pose and tendon forces) to move sequentially through the poses associated with the given state-flow map. Specifically, in the reposed series of poses (S1-S4), contraction of the ventral forearm musculature initially provides proportional, direct velocity control of the flexion of the middle, ring, and little fingers. In the absence of an object in the hand device, continued flexion of the ventral forearm musculature will bring these fingers into the palm, such that the hand device assumes a pointing pose (S2). Once these fingers reach the palm (as detected by sensors in the device), the controller switches the direct velocity EMG control to the index finger, such that continued contraction of the ventral musculature provides proportional, direct velocity control of index finger flexion. Once the index finger contacts the palm (as detected by sensors in the hand hand device) the hand device assumes a hook pose (S3). Thereafter, the controller switches the direct velocity EMG control to thumb flexion, such that continued contraction of the ventral musculature provides proportional, direct velocity control of thumb flexion to reach the lateral pinch pose (S4). Thus, when starting from the reposed platform pose (S1) with no object in the hand device, a brief contraction of the ventral forearm musculature will result in a pointing pose (S2), while a longer contraction will result in the direct EMG control of a key or lateral pinch pose (S4). Correspondingly, a continued contraction of the antagonist (dorsal forearm) musculature will release the key or lateral pinch pose (S4) and eventually return the device to the open, platform grasp with the thumb in a reposed position.

In the case that an object (e.g., the handle of a suitcase or other object) is present in the hand device (at pose 51) when the contraction of the ventral forearm musculature occurs, the device will first close the middle, ring, and little fingers around the object (e.g., suitcase handle) to reach a grasping point pose (S2). Once sensors in the hand device detect that these fingers have grasped the object, direct control from the ventral/dorsal musculature switches to the index finger, and thus continued flexion of the ventral musculature will flex the index finger around the handle, thus forming a grasping hook pose (S3). Once sensors detect that the index finger has completed the grasping hook pose, direct control is switched to the thumb to provide a grasping pinch pose (S4). Thus, if starting from the reposed configuration, a grasping hook pose (S3) is achieved with a simple contraction of the ventral musculature of the forearm, and is released with a simple contraction of the antagonist musculature (which if sustained will return the hand device to the reposed platform pose (S1)).

If the user selects the opposed configuration for the thumb (by co-contracting the forearm musculature when in the reposed platform configuration), the hand device switches to the opposed sequence of poses (from 302 to 304), starting with the opposed platform pose (S5). In the opposed sequence, flexion of the ventral forearm musculature brings the thumb and index finger together under the direct, proportional control to form a tip pose (S6), while flexion of the dorsal musculature brings them apart. Once a tip pose (S6) is achieved, continued flexion of the ventral musculature will switch direct EMG control to the middle, ring, and little fingers to achieve a cylindrical/tip pose (S7). In the case that the hand device is grasping an object from the opposed platform pose (S5), contraction of the ventral forearm musculature will initially provide direct control of simultaneous index finger and thumb flexion to achieve a grasping tip pose (S6). Once sensors detect these digits have grasped the object, direct control switches to the middle, ring, and little fingers. Continued flexion of the ventral forearm musculature brings these fingers into contact with the object being grasped, and thus results in either a cylindrical, spherical, or tripod pose for grasping (S7), also known as chuck grasp. Whether the pose at S7 is cylindrical, spherical, or tripod depends on the geometry of the object (i.e., the same control pathway is utilized for all three grasps). Thus, when starting from the opposed platform pose (S5), a brief contraction of the ventral forearm musculature will result in a tip pose (S6), while a longer contraction will result in a cylindrical, spherical, or tripod pose (S7), depending on the shape of the object. Correspondingly, contraction of the antagonist (dorsal forearm) musculature will release the current pose and return the hand device to the opposed platform pose (S5).

Although the description above refers to detection of an object being grasped to determine how to configure the chuck grasp, the chuck grasp can also be configured based on other criteria. For example, the hand device can be configured to detect at least one of a hindrance to motion, a grasping force, an acceleration, or an angular velocity for the plurality of joints to yield a detected force. The detected force can then be used to control the configuration or the chuck grasp. Further, selection of different grasp configuration is not limited solely to the chuck grasp pose (S7). Rather, alternate configuration for any of the poses in FIG. 3 can be provided in response to detection of a force, object, or the like.

In the various embodiments, the EMG signals can be obtained from any location. However, specific configuration can be selected in some embodiments. For example, the EMG signals can be acquired from a plurality of intramuscular and/or surface electrodes on ventral and dorsal muscle sites of forearm. In another example, the EMG signals can also acquired from a plurality of intramuscular and/or surface electrodes on ventral and dorsal muscle sites of a humerus. In yet another example, such as in the case of a transhumeral amputee, the flexion and extension EMG measurements correspond to measurement of the biceps and triceps muscles, respectively.

In some embodiments, threshold levels for initiating a transition can be specified on a directional basis. These threshold levels can be based on magnitude or time. That is, to cause motion in a direction, only a single threshold value is needed for the direction, irrespective of the mechanical state. Thus, a signal with a sufficiently high intensity or sufficiently long duration will initiate the transition. However, in some embodiments, finer control of the transitions between poses may be desired. In such embodiments, as shown in FIG. 3, pose by pose threshold values (Th, where, i=1, 2, ... 10) can be defined. Furthermore, as shown in FIG. 3, the threshold values need not be symmetric for different types of motion along a same direction or between proximal poses. Such a configuration allows the transitions to be further customized for particular transitions or for particular users.

In some embodiments the control system can also be configured to trigger an automatic transition to a pose. For example, in one embodiment of the invention, two threshold values for a same direction along a motion axis can be provided for a same transition. The first threshold value can be provided to allow continuous control of the transition. That is, the motion proceeds as long as the input control signal meets the threshold level. The second threshold value can be used to trigger a complete transition to the next pose. Such a configuration can be advantageous as it can allow a user to transition between multiple states using less signals and less effort.

An exemplary arrangement using thresholds to determine whether a transition between pose should occur is illustrated in FIG. 3 and described below with respect to a hand device configured with four actuators: A1 (index finger (DII) flexion/extension actuator), A2 (middle, ring, and little finger (DIII-V) flexion/extension actuator), A3 (thumb (D1) flexion/extension actuator), and A4 (thumb (D1) abduction/adduction actuator). Thus, the conditions for actuating are as follows:

a. S1 TO S2→A2D>Th OR A2F>Th: The force or displacement for the middle, ring, and little finger actuator (A2F, A2D, respectively) should be greater than a threshold (Th).
b. S2 TO S3 A1D>Th OR A1F>Th: The force or displacement for the index finger actuator (A1F, A1D, respectively) should be greater than a threshold (Th).
c. S3 TO S4→A3D>Th: The displacement for the thumb flexion/extension actuator (A3D) should be greater than a threshold (Th).
d. S4 TO S3→A3D<Th: The displacement for the thumb flexion/extension actuator (A3D) should be less than a threshold (Th).
e. S3 TO S2→MD<Th: The displacement for the index finger actuator (A1D) should be less than a threshold (Th).
f. S2 TO S1→A2D<Th: The displacement for the middle, ring, and little finger actuator (A2D) should be less than a threshold (Th).
g. S5 TO S6→MD>Th AND A3D>Th: The displacement for the index finger actuator (A1D) and the thumb flexion/extension actuator (A3D) should both be greater than a threshold (Th).
f. S6 TO S7→A2D>Th OR A2F>Th: The force or the displacement for the middle, ring, and little finger finger actuator (A2F, A2D, respectively should both be greater than a threshold (Th).
g. S7 TO S6→A2D<Th: The displacement for the middle, ring, and little finger actuator (A2D) should be less than a threshold (Th).
f. S6 TO S5→MD<Th AND A3D<Th: The displacement for the index finger actuator (A1D) and the thumb flexion/extension actuator (A3D) should both be less than a threshold (Th).
g. S1 to S5 or S5 to S1→A co-contraction signal greater than a threshold (Th) is detected.

It is worth noting that each pose is not a fixed configuration of digits, but rather a combination of digits at fixed positions and digits controllable by the user. Thus, during each state, one or more actuators can remain active for the user to control. FIG. 3 shows, in white lettering for each pose, an exemplary arrangement of the actuators that are active within each pose. For example, in the point posture (S2), EMG flexion and extension commands correspond to movement of actuators A1 and A2. That is, in the pointing posture, a flexion command flexes digit II (the forefinger) via actuator A1, while an extension command extends digit II via A1. In the case that digit II is fully extended, an extension command corresponds to extension of digits III-V via actuator A2, while a flexion command corresponds to the flexion of these fingers via A2. Similarly, the other indicated digits can be actuated in the other poses.

In an alternate embodiment, rather than using an EMG "co-contraction" response to switch automatically between the opposition and reposition poses (and associated sequences of poses), this function can be performed by using the same (differential) flexion and extension contractions that are used to move along the sequence of poses. That is, a continuous extension EMG input will drive the hand device into full extension, in either the opposed or reposed thumb poses. If in the reposed thumb pose, a continued extension input will move the thumb (in a proportional manner) to the opposed pose. If the thumb does not reach full opposition, the thumb can be proportionally positioned by using both extension/flexion to move it in the opposition/reposition direction. Once the thumb is moved into the fully opposed configuration, a flexion input will move the hand device along the opposition sequence of poses. Once fully extended, a continued extension will move the thumb (in a proportional manner) to the reposed pose. With this approach, thumb opposition/reposition can be controlled proportionally, and no "co-contraction" response is required for hand control. This approach can be referred to as a "pure differential" approach.

In yet another embodiment, either the "co-contraction" or "pure differential" approaches can be supplemented with a virtual detent feature between poses. This feature will prevent continuous switching from one pose to the next. Instead, a continuous contraction will drive the hand device to the next contiguous pose. In order to continue into the following pose, the user will be required to relax, such that there is a temporary pause in the measured differential EMG, then resume the contraction, which will move the hand device past the "virtual detent" and into the next configuration. This can alternatively be considered a "ratcheting" approach, since each contraction only moves the user to the next contiguous pose. Moving into a subsequent pose requires another distinct contraction.

The thresholds described above can be additionally utilized to provide additional functionality or alternate versions of a pose in the various embodiments. In particular, the thresholds can be utilized not only to transition between states in a state flow map, but can also be used to trigger transitions to alternate versions of a pose. For example, to pick up an small object using the map 300, the user would configure the hand device to start at the platform opposition state (S5) and transition to the tip state (S6) to grasp the small object using the index finger and thumb. However, as shown in FIG. 3, the middle, ring, and little fingers would remain extended and the extension of these fingers may interfere with properly grasping the small object. Therefore, it might be preferable for these fingers to be closed prior to grasping the object, as typical for a natural hand. Accordingly, in some embodiments, an alternate version of a pose can be provided when EMG signals indicate that the user is trying to perform a task requiring precision or some care. This can be based on a magnitude of the EMG signals. For example, when a low magnitude of EMG is detected, not only can the velocity of the joints be changed, but can also be triggered to close the middle, ring, and little fingers. A similar configuration can be provided for any of the other poses.

Figure 4:
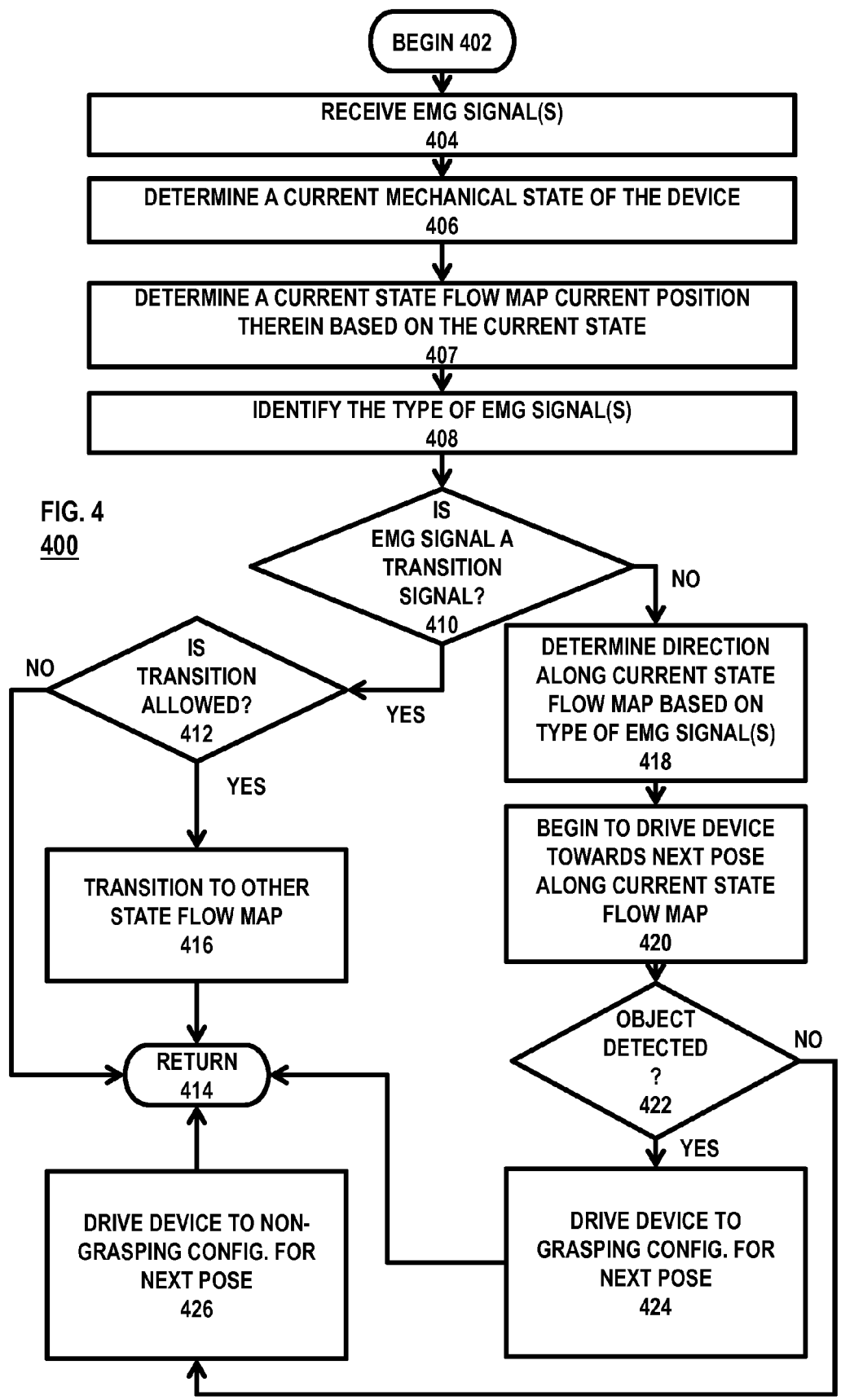
FIG. 4 shows a flow chart of steps in an exemplary method for operating a control system for a hand device in accordance with an embodiment of the invention.

Using a topographic map in accordance with the various embodiments, a control system for a hand device can be configured to use the map to control operation of the hand device. An exemplary method 400 for controlling such devices is shown in FIG. 4. Method 400 begins at block 402 and proceeds to block 404. At block 404, EMG signal(s) are received. As noted above, the user provides EMG signals associated with motion in a particular direction in the topographic state map. For example, referring back to FIG. 3, a control signal can be received that is associated with flexion or extension, indicating that a user wishes to perform extension or flexion of the digits in hand device 100.

Subsequently or concurrently with block 404, the current mechanical state of the hand device is determined at block 406. In general, the current mechanical state of a device refers to the current configuration of the joints in the hand device. In the various embodiments of the invention, this configuration can be determined directly or indirectly, depending on the sensors available in the device. For example, some devices can include sensors at some or each of the joints, sensors at all or some of the force actuators, or any combination thereof. One of ordinary skill in the art will recognize that since continuous control is provided in the various embodiments of the invention, in many cases the mechanical state of the device may not correspond to one of the poses. That is, a current configuration of the device may be a configuration of joints falling between two of the poses.

Once the mechanical state of the device is determined at block 406, the current state flow map and the current position therein are determined at block 407. For example, the current state flow map could be determined based on the configuration of thumb. That is, based on whether the thumb is opposed or reposed. However, the various embodiments are not limited in this regard and the current state flow map can be determined on the configuration of other digits of the hand device as well.

With respect to a current position within the current state map, this can be determined in various ways. For example, as described above, a transition between control of digits begins when a set digits reach a position that signals that control should be shifted to a different set of digits. Accordingly, the current state can be determined based on whether the digits of the hand device meet one of these positions associated with a pose. Additionally, the position between poses can be further detected by determining the extent to which the digits being control have reached a next position associated with a next pose. However, various other ways for determining the current position can be provided, including using matching or calculating of position based on a current configuration of the hand device and the current state flow map.

Once the current state flow map and current position are determined at step 407, the type of EMG signals received can be determined at step 408. That is, a determination can be made whether the signal is one indicating flexion or extension or whether the signal is a co-contraction or other type of pre-defined transition signal for switching between state flow maps.

If it is determined at step 410 that the EMG signal is a transition signal for switching between state flow maps, the method proceeds to step 412. At step 412, it is determined whether a transition is currently allowed based on the current mechanical state. That is, referring back to FIG. 3, whether the hand device is in one of the opposed or reposed platform positions. In some embodiments, other transitions can be allowed as well that do not occur at the platform positions. If the transition is not allowed, the method 400 returns to previous processing at step 414, including repeating method 400. If the transition is allowed at step 412, the hand device transitions to control under the other state flow map at block 416. This can also include adjusting the hand device. For example, when transitioning between the reposed and opposed state flow maps, the transition can include adjusting the position of the thumb accordingly. Once the transition is complete, the method 400 returns to previous processing at step 414, including repeating method 400.

If it is determined at step 410 that the EMG signals are not transition signals for switching between state flow maps, the method proceeds instead to step 418. That is, the EMG signals provided are for flexion or extension of the hand device. At step 418, based on the EMG signals, the direction for adjusting the hand device is determined. For example, the EMG signals may indicate extension to release or extend the digits or the EMG signal may indicate flexion to grasp an object or close the digits of the hand device. Once the direction is determined at step 418, the hand device can be driven towards the next pose in the current state map at block 420.

As noted above, the hand device can respond differently if grasping an object. Accordingly, if an object is detected at step 422, the hand device can be driven towards the grasping configuration for a next pose at step 424. This can include detection of the shape of the object as described above. If no object is detected at step 422, the hand device can be driven towards the grasping configuration for a next pose at step 424. In some embodiments, the device is only driven to the next pose as long as the EMG signal(s) is maintained. However, in other embodiments, as described above, it is not necessary to maintain the EMG signal(s) and the controller can automatically proceed to the next pose. Following either of steps 424 and 426, the method 400 returns to previous processing at step 414, including repeating method 400.

Although FIG. 4 is described with respect to responding to an object, the various embodiments are not limited in this regard. Rather, the same methodology can be used to adjust the grasp or pose based on any hindrance or force detected by the sensors in a hand device.

Figure 5:
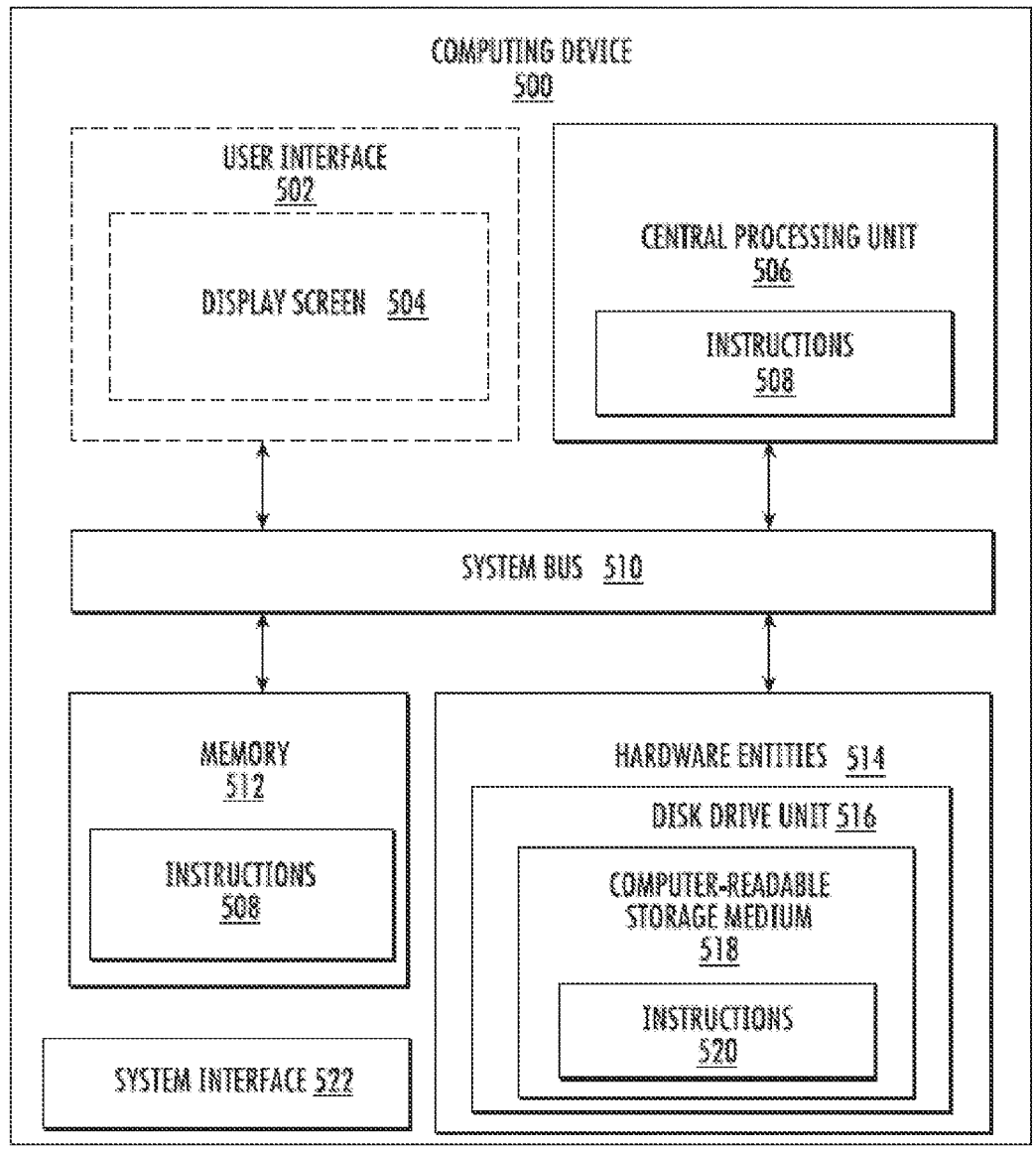
FIG. 5 is block diagram of a computing device which can be implemented as control system in accordance with an embodiment of the invention.

Referring now to FIG. 5, there is provided a detailed block diagram of a computing device 500 which can be implemented as a control system in accordance with an embodiment of the invention. Although various components are shown in FIG. 5, the computing device 500 may include more or less components than those shown in FIG. 5. However, the components shown are sufficient to disclose an illustrative embodiment of the invention. The hardware architecture of FIG. 5 represents only one embodiment of a representative computing device for controlling a jointed mechanical device.

As shown in FIG. 5, computing device 500 includes a system interface 522, a Central Processing Unit (CPU) 506, a system bus 510, a memory 512 connected to and accessible by other portions of computing device 500 through system bus 510, and hardware entities 514 connected to system bus 510. At least some of the hardware entities 514 perform actions involving access to and use of memory 512, which may be any type of volatile or non-volatile memory devices. Such memory can include, for example, magnetic, optical, or semiconductor based memory devices. However the various embodiments of the invention are not limited in this regard.

In some embodiments, computing system can include a user interface 502. User interface 510 can be an internal or external component of computing device 500. User interface 502 can include input devices, output devices, and software routines configured to allow a user to interact with and control software applications installed on the computing device 500. Such input and output devices include, but are not limited to, a display screen 504, a speaker (not shown), a keypad (not shown), a directional pad (not shown), a directional knob (not shown), and a microphone (not shown). As such, user interface 502 can facilitate a user-software interaction for launching software development applications and other types of applications installed on the computing device 500.

System interface 522 allows the computing device 500 to communicate directly or indirectly with the other devices, such as an external user interface or other computing devices. Additionally, computing device can include hardware entities 514, such as microprocessors, application specific integrated circuits (ASICs), and other hardware. As shown in FIG. 5, the hardware entities 514 can also include a removable memory unit 516 comprising a computer-readable storage medium 518 on which is stored one or more sets of instructions 520 (e.g., software code) configured to implement one or more of the methodologies, procedures, or functions described herein. The instructions 520 can also reside, completely or at least partially, within the memory 512 and/or within the CPU 506 during execution thereof by the computing device 500. The memory 512 and the CPU 506 also can constitute machine-readable media.

While the computer-readable storage medium 518 is shown in an exemplary embodiment to be a single storage medium, the term "computer-readable storage medium"

should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure.

The term "computer-readable storage medium" shall accordingly be taken to include, but not be limited to solid-state memories (such as a memory card or other package that houses one or more read-only (non-volatile) memories, random access memories, or other re-writable (volatile) memories), magneto-optical or optical medium (such as a disk or tape). Accordingly, the disclosure is considered to include any one or more of a computer-readable storage medium or a distribution medium, as listed herein and to include recognized equivalents and successor media, in which the software implementations herein are stored.

System interface 522 can include a network interface unit configured to facilitate communications over a communications network with one or more external devices. Accordingly, a network interface unit can be provided for use with various communication protocols including the IP protocol. Network interface unit can include, but is not limited to, a transceiver, a transceiving device, and a network interface card (NIC).

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the invention.

FIGS. 6A-6C provide data from operation of a hand device, as controlled using the state map in FIG. 3. Specifically, FIG. 6 shows the coordinated motion of multiple actuators based on the two unipolar flexion and extension inputs, measured from EMG electrodes on the ventral and dorsal aspects, respectively, of a subject's forearm. FIG. 6A is an X-Y plot of EMG input as a function of time. As described above, a co-contraction response is used to switch between the opposition and reposition thumb poses. FIG. 6B is an X-Y plot of hand state or pose as a function of time, showing targeted (dashed line) and actual (solid line) poses. FIG. 6C is an X-Y plot of normalized digit displacement as a function of time for actuators A1 (index finger (DII) flexion/extension actuator), A2 (middle, ring, and little finger (DIII-V) flexion/extension actuator), A3 (thumb (D1) flexion/extension actuator), and A4 (thumb (D1) abduction/adduction actuator). Similar to FIG. 6B, FIG. 6C compares targeted (dashed line) and actual (solid line) displacement for each of the actuators as a function of time. As shown in FIGS. 6B and 6C, the targeted and actual pose and displacement compare favorably.

Figure 7A:
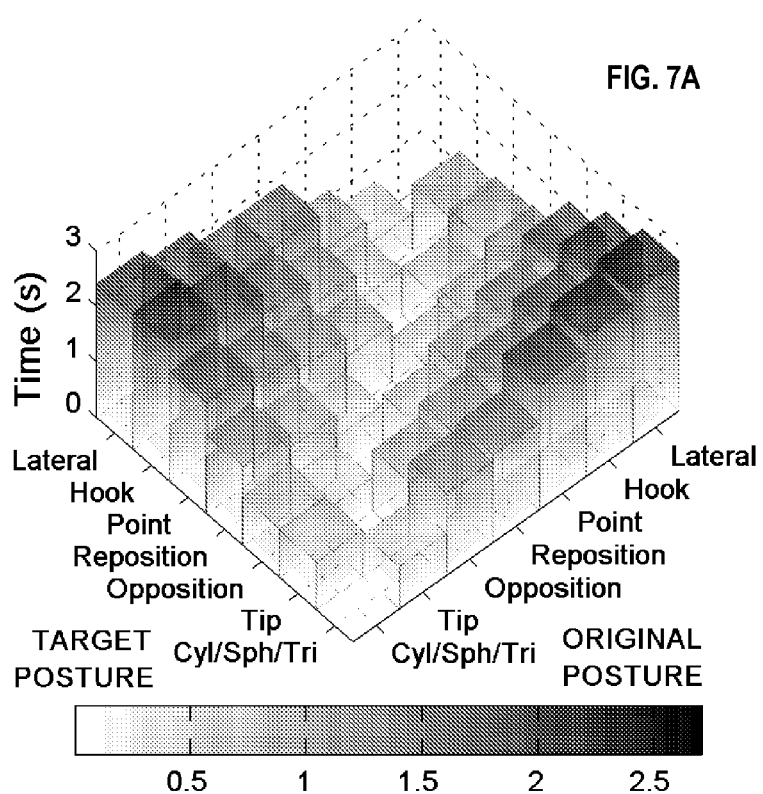
FIGS. 7A and 7B are 3-D bar graphs illustrating the performance of the hand device, as controlled using the state map in FIG. 3, and the performance of the natural hand (as measured with a data glove), respectively.
Figure 7B:
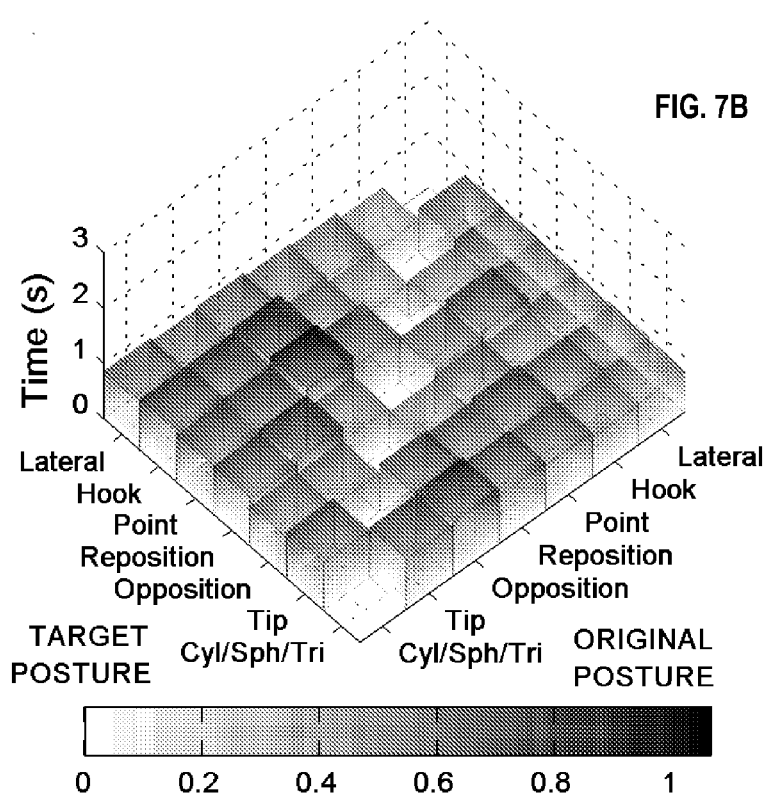

FIGS. 7A and 7B are 3-D bar graphs illustrating the performance of the hand device, as controlled using the state map in FIG. 3, and the performance of the natural hand (as measured with a dataglove), respectively. In each 3-D bar graph, the time required to reach a given desired pose from any given original pose is indicated by the height and color of the bar located at the intersection of those poses. These graphs are based on the data displayed in Tables 1 and 2. These data indicate that for the natural hand, the average time to reach any pose from any other is 0.81 sec. For a hand device configured in accordance with an embodiment of the invention, the average time to reach any pose from any other is 1.49 sec. For transitions between adjacent poses, the average time was 0.89 sec, which is closely matched to the native hand. This shows that the control methodology in accordance with the various embodiments compares favorably with the natural hand.

TABLE 1

Average transition times of all subjects between different poses for the native hand*.

| | | Target Pose | | | | | | |
|---|---|---|---|---|---|---|---|---|
| | | Lateral | Hook | Point | Reposition | Opposition | Tip | Cyl/Sph/Tri |
| Original Pose | Lateral | | 0.81 (0.36) | 0.81 (0.36) | 0.79 (0.36) | 0.76 (0.50) | 0.78 (0.25) | 0.74 (0.21) |
| | Hook | 0.59 (0.12) | | 0.69 (0.25) | 0.90 (0.65) | 0.67 (0.19) | 0.80 (0.28) | 0.72 (0.19) |
| | Point | 0.72 (0.31) | 0.62 (0.15) | | 0.81 (0.60) | 0.73 (0.19) | 0.88 (0.26) | 0.82 (0.28) |
| | Repos. | 0.76 (0.25) | 0.72 (0.18) | 0.86 (0.48) | | 0.65 (0.28) | 0.82 (0.50) | 0.86 (0.22) |
| | Oppos. | 0.82 (0.30) | 1.02 (0.48) | 1.06 (0.53) | 0.71 (0.19) | | 0.89 (0.30) | 0.97 (0.38) |
| | Tip | 0.77 (0.12) | 0.94 (0.47) | 0.90 (0.33) | 0.96 (0.33) | 0.71 (0.23) | | 0.91 (0.39) |
| | Cyl/Sph/Tri | 0.85 (0.42) | 0.92 (0.33) | 0.86 (0.31) | 0.86 (0.27) | 0.72 (0.15) | 0.84 (0.24) | |

*Standard deviations are displayed in parenthesis.

TABLE 2

Average transition times of all subjects between different poses for multigrasp myoelectric control*.

|  |  | Target Pose | | | | | | |
|---|---|---|---|---|---|---|---|---|
|  |  | Lateral | Hook | Point | Reposition | Opposition | Tip | Cyl/Sph/Tri |
| Original Pose | Lateral |  | 1.20 (0.63) | 1.32 (0.53) | 1.37 (0.21) | 2.02 (0.70) | 2.43 (0.68) | 2.70 (0.69) |
|  | Hook | 0.67 (0.14) |  | 0.89 (0.29) | 1.05 (0.14) | 1.60 (0.39) | 2.03 (0.51) | 2.50 (0.95) |
|  | Point | 1.12 (0.35) | 0.84 (0.22) |  | 0.81 (0.43) | 1.25 (0.36) | 1.67 (0.32) | 2.21 (0.50) |
|  | Repos. | 1.82 (0.96) | 1.34 (0.36) | 1.02 (0.31) |  | 0.92 (0.51) | 1.36 (0.51) | 1.57 (0.56) |
|  | Oppos. | 1.84 (0.44) | 1.79 (0.56) | 1.38 (0.43) | 0.75 (0.26) |  | 1.11 (0.43) | 1.47 (0.88) |
|  | Tip | 2.16 (0.44) | 2.18 (0.56) | 1.68 (0.38) | 1.15 (0.44) | 0.61 (0.13) |  | 0.75 (0.10) |
|  | Cyl/Sph/Tri | 2.40 (0.40) | 2.46 (0.61) | 1.97 (0.55) | 1.40 (0.37) | 0.88 (0.17) | 0.85 (0.22) |  |

*Standard deviations are displayed in parenthesis.

Applicants present certain theoretical aspects above that are believed to be accurate that appear to explain observations made regarding embodiments of the invention. However, embodiments of the invention may be practiced without the theoretical aspects presented. Moreover, the theoretical aspects are presented with the understanding that Applicants do not seek to be bound by the theory presented.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application. For example, one alteration or modification includes configuring the hand device such that it can only switch between a portion of the poses in a state flow map under certain conditions. For example, if signal intensity or signal time is too low or too high, the amount of switching can be limited. Yet another alteration or modification includes utilizing the co-contraction for multiple purposes. For example, a prostheses or exoskeleton having a powered hand and powered elbow can be configured such that the co-contraction of the muscles toggles the control of the prosthesis between the elbow joint and hand.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A method for operating a grasping device using a plurality of parallel, bi-directional state flow maps each defining a sequence of poses for a plurality of joints in the grasping device, the method comprising:
   receiving at least one control signal;
   determining a current pose of the grasping device within the one of the plurality of state flow maps currently selected for the grasping device; and
   selectively actuating the plurality of joints to traverse the sequence of poses, wherein a direction for traversing the sequence of poses is based on the at least one control signal,
   wherein a first of the plurality of state flows comprises a sequence comprising a platform pose with the thumb in repose, a pointing pose, a hook pose, and a lateral pinch pose.

2. The method of claim 1, wherein selectively actuating the plurality of joints further comprises automatically transitioning to a next one of the sequence of poses in the direction if the at least one control signal meets a threshold criteria based on at least one of an intensity and a length of the at least one signal.

3. The method of claim 1, wherein the actuating of the plurality of joints further comprises:
   detecting a hindrance to motion for the plurality of joints; and
   adjusting an amount of actuating allowed for the plurality of joints between the sequence of poses based on a magnitude of the hindrance.

4. The method of claim 1, wherein the actuating of the plurality of joints further comprises:

measuring a grasping force; and adjusting an amount of actuating allowed for the plurality of joints between the sequence of poses based on a magnitude of the grasping force.

5. The method of claim 1, wherein the actuating of the plurality of joints further comprises:

measuring at least one of an acceleration or an angular velocity of the grasping device and adjusting an amount of actuating allowed for the plurality of joints between the sequence of poses based on a magnitude of the acceleration or the angular velocity.

6. The method of claim 1, wherein the at least one control signal is based on an at least one electromyogram (EMG) signal.

7. The method of claim 6, wherein the at least one EMG signal is received from first and second channels of EMG signals, wherein the first channel of EMG signals is used to provide control signals for traversing the plurality of poses in a first direction and the second channel of EMG signals is used to provide control signals for traversing the plurality of poses in a second direction opposite to the first direction.

8. The method of claim 6, wherein if a magnitude of the at least one EMG signal falls below a transition threshold for the current pose, an alternate version of the current pose is selected.

9. The method of claim 1, wherein prior to the selective actuating of the plurality of joints, the method further comprises:

ascertaining whether the at least one control signal is a transition signal; and when the at least one control signal is a transition signal and the current pose is a transition pose within the one of the plurality of state flow maps, selecting a different one of the plurality of state flow maps for the grasping device.

10. The method of claim 9, wherein the switching between state-flow maps results in an automated repositioning of the hand from the transition pose in one of the plurality of state flow maps to a corresponding transition pose in the different one of the plurality of state flow maps.

11. The method of claim 1, wherein a second of the plurality of state flows comprises a sequence comprising a platform pose with the thumb in opposition, a tip pose, and a chuck pose.

12. The method of claim 11, wherein the grasping device can only switch between the first of the plurality of state flow maps and the second of the plurality of state flow maps only from corresponding platform poses.

13. A grasping device, comprising:

a plurality of joints;

a memory for storing a plurality of parallel, bi-directional state flow maps that each defining a sequence of poses for the plurality of joints; and a processor communicatively coupled to the memory and the plurality of joints, wherein the processor is configured for:

receiving at least one control signal;

determining a current pose of the grasping device within the one of the plurality of state flow maps currently selected for the grasping device; and selectively actuating the plurality of joints to traverse the sequence of poses, wherein a direction for traversing the sequence of poses is based on the at least one control signal, wherein a first of the plurality of state flows comprises a sequence comprising a platform pose with the thumb in repose, a pointing pose, a hook pose, and a lateral pinch pose, a second of the plurality of state flows comprises a sequence comprising a platform pose with the thumb in opposition, a tip pose, and a chuck pose, and wherein the grasping device can only switch between the first of the plurality of state-flow maps and the second of the plurality of state-flow maps only from corresponding platform poses.

14. The device of claim 13, wherein the processor is further configured for selectively actuating the plurality of joints further comprises automatically transitioning to a next one of the sequence of poses in the direction if the at least one control signal meets a threshold criteria based on at least one of an intensity and a length of the at least one signal.

15. The device of claim 13, wherein the actuating of the plurality of joints further comprises:

detecting at least one of a hindrance to motion, a grasping force, an acceleration, or an angular velocity for the plurality of joints to yield a detected force; and adjusting an amount of actuating allowed for the plurality of joints between the sequence of poses based on a magnitude and a type of the detected force.

16. The device of claim 13, wherein the at least one control signal is based on an at least one electromyogram (EMG) signal.

17. The device of claim 13, wherein prior to the selective actuating of the plurality of joints, the method further comprises:

ascertaining whether the at least one control signal is a transition signal; and when the at least one control signal is a transition signal and the current pose is a transition pose within the one of the plurality of state flow maps, selecting a different one of the plurality of state flow maps for the grasping device and automatically repositioning of the hand from the transition pose in one of the plurality of state flow maps to a corresponding transition pose in the different one of the plurality of state flow maps.

18. A grasping device, comprising:

a plurality of joints;

a memory for storing a plurality of parallel, bi-directional state flow maps that each defining a sequence of poses for the plurality of joints; and a processor communicatively coupled to the memory and the plurality of joints, wherein the processor is configured for:

receiving at least one control signal;

determining a current pose of the grasping device within the one of the plurality of state flow maps currently selected for the grasping device; and selectively actuating the plurality of joints to traverse the sequence of poses, wherein a direction for traversing the sequence of poses is based on the at least one control signal, wherein the at least one control signal is based on an at least one electromyogram (EMG) signal, wherein the at least one EMG signal is received from first and second channels of EMG signals, wherein the first channel of EMG signals is used to provide control signals for traversing the plurality of poses in a first direction and the second channel of EMG signals is used to provide control signals for traversing the plurality of poses in a second direction opposite to the first direction, and wherein a co-contraction in at least one of the first and second channels of EMG is used to provide control signals for transitioning between different ones of the plurality of state flow maps.

* * * * *